US011318144B2

(12) United States Patent
Wang et al.

(10) Patent No.: US 11,318,144 B2
(45) Date of Patent: *May 3, 2022

(54) COMPOSITIONS AND METHODS FOR TREATING ALZHEIMER'S DISEASE AND PARKINSON'S DISEASE

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/913,927

(22) Filed: Jun. 26, 2020

(65) Prior Publication Data

US 2020/0323873 A1    Oct. 15, 2020

Related U.S. Application Data

(63) Continuation-in-part of application No. 16/382,885, filed on Apr. 12, 2019.

(51) Int. Cl.
*A61K 31/55*     (2006.01)
*A61K 31/714*    (2006.01)
*A61K 9/00*      (2006.01)

(52) U.S. Cl.
CPC ............ *A61K 31/55* (2013.01); *A61K 31/714* (2013.01); *A61K 9/0053* (2013.01)

(58) Field of Classification Search
None
See application file for complete search history.

(56) References Cited

U.S. PATENT DOCUMENTS

| | | |
|---|---|---|
| 5,068,233 A | 11/1991 | Achterrath-Tuckerman et al. |
| 5,086,050 A | 2/1992 | Hettche et al. |
| 5,110,814 A | 5/1992 | Engel et al. |
| 5,994,357 A | 11/1999 | Theoharides |
| 6,008,221 A | 12/1999 | Smith et al. |
| 6,017,909 A | 1/2000 | Hettche et al. |
| 6,255,294 B1 * | 7/2001 | Armstrong ............ A61P 37/00 514/52 |
| 6,849,621 B2 | 2/2005 | Rosenblum et al. |
| 7,022,687 B1 | 4/2006 | Szelenyi et al. |
| 7,220,735 B2 | 5/2007 | Ting et al. |
| 7,355,042 B2 | 4/2008 | Edgar et al. |
| 7,384,981 B2 | 6/2008 | Kiliaan et al. |
| 7,615,550 B2 | 11/2009 | Heightman et al. |
| 7,786,161 B2 | 8/2010 | Tani et al. |
| 7,888,391 B2 | 2/2011 | Kiliaan et al. |
| 8,071,073 B2 * | 12/2011 | Dang ............ A61P 27/16 424/45 |
| 8,168,620 B2 | 5/2012 | Lulla et al. |
| 8,304,405 B2 | 11/2012 | Lulla et al. |
| 8,318,709 B2 | 11/2012 | Lulla et al. |
| 8,362,078 B2 | 1/2013 | Kiliaan et al. |
| 8,372,451 B2 | 2/2013 | Vuckovic |
| 8,440,243 B2 | 5/2013 | Maewal |
| 8,741,319 B2 | 6/2014 | Crain et al. |
| 8,758,816 B2 | 6/2014 | Fuge et al. |
| 8,859,531 B2 | 10/2014 | Lee et al. |
| 8,865,733 B2 | 10/2014 | Felder |
| 9,278,092 B2 | 3/2016 | Chase et al. |
| 9,308,223 B2 | 4/2016 | Maewal |
| 9,504,712 B2 | 11/2016 | Kiliaan et al. |
| 9,662,359 B2 | 5/2017 | Vuckovic |
| 9,844,525 B2 | 12/2017 | Kiliaan et al. |
| 9,901,585 B2 | 2/2018 | Lulla et al. |
| 9,919,050 B2 | 3/2018 | Dang et al. |
| 10,639,314 B1 | 5/2020 | Wang et al. |
| 10,639,315 B1 | 5/2020 | Wang et al. |
| 10,639,316 B1 | 5/2020 | Wang et al. |
| 10,898,493 B2 | 1/2021 | Wang et al. |
| 10,946,026 B2 | 3/2021 | Wang et al. |
| 10,966,989 B2 | 4/2021 | Wang et al. |
| 11,116,773 B2 | 9/2021 | Wang et al. |
| 2003/0229030 A1 | 12/2003 | Theoharides |
| 2005/0163843 A1 | 7/2005 | Boehm et al. |
| 2006/0051416 A1 | 3/2006 | Rastogi et al. |
| 2009/0012039 A1 | 1/2009 | Kurtz |
| 2009/0318703 A1 | 12/2009 | Tani et al. |
| 2010/0152108 A1 | 6/2010 | Hung et al. |

(Continued)

FOREIGN PATENT DOCUMENTS

| | | |
|---|---|---|
| AU | 2019443520 A1 | 12/2021 |
| AU | 2019445048 A1 | 12/2021 |

(Continued)

OTHER PUBLICATIONS

Hua S. "Advances in Nanoparticulate Drug Delivery Approaches for Sublingual and Buccal Administration". Nov. 10, 2019. (Article 1328). pp. 1-9. (Year: 2019).*
Bartlett et al. "Rhinorrhea as a Result of Alzheimer's Disease Treatment: A Case Report". The Senior Care Pharmacist. Dec. 2019; 34(10):669-673. (Year: 2019).*
Ancill et al. "Agitation in the Demented Elderly: A Role for Benzodiazepines?" International Clinical Psychopharmacology, 1991; 6:141-146.
Co-Pending U.S. Appl. No. 16/424,788, Final Office Action dated Aug. 28, 2020, 17 pages.
Co-Pending U.S. Appl. No. 16/424,788, Response to Aug. 28, 2020 Final Office Action filed Oct. 19, 2020, 6 pages.
Co-Pending U.S. Appl. No. 16/884,459, Non-Final Office Action dated Aug. 11, 2020, 35 pages.
Co-Pending U.S. Appl. No. 16/884,553, Non-Final Office Action dated Aug. 11, 2020, 26 pages.
Cummings et al. "Effect of Dextromethorphan-Quinidine on Agitation in Patients with Alzheimer Disease Dimentia: A Randomized Clinical Trial". JAMA, 2015; 314(12):1242-1254.

(Continued)

*Primary Examiner* — Leslie A. Royds Draper
(74) *Attorney, Agent, or Firm* — New River Valley IP Law, P.C.; Michele L. Mayberry

(57) ABSTRACT

Pharmaceutical compositions comprising azelastine, or a pharmaceutically acceptable salt of azelastine, and methylcobalamin are disclosed. Methods of using the pharmaceutical compositions for treating patients with Alzheimer's disease or Parkinson's disease are also disclosed.

14 Claims, No Drawings

(56) References Cited

U.S. PATENT DOCUMENTS

| | | | |
|---|---|---|---|
| 2010/0168053 A1* | 7/2010 | Kurtz | A61K 31/519 514/52 |
| 2012/0237570 A1 | 9/2012 | Crain et al. | |
| 2013/0252929 A1 | 9/2013 | Lee et al. | |
| 2014/0127328 A1 | 5/2014 | Crain et al. | |
| 2014/0158117 A1 | 6/2014 | Dang et al. | |
| 2015/0216849 A1 | 8/2015 | Dedhiya et al. | |
| 2017/0035780 A1 | 2/2017 | Lulla et al. | |
| 2018/0104294 A1 | 4/2018 | Vuckovic | |
| 2018/0116979 A1 | 5/2018 | Clarence-Smith et al. | |
| 2020/0323867 A1 | 10/2020 | Wang et al. | |
| 2020/0323868 A1 | 10/2020 | Wang et al. | |
| 2020/0323870 A1 | 10/2020 | Wang et al. | |
| 2020/0323871 A1 | 10/2020 | Wang et al. | |
| 2020/0323876 A1 | 10/2020 | Wang et al. | |
| 2020/0323877 A1 | 10/2020 | Wang et al. | |
| 2021/0069209 A1 | 3/2021 | Wang et al. | |
| 2022/0000882 A1 | 1/2022 | Wang et al. | |

FOREIGN PATENT DOCUMENTS

| | | | |
|---|---|---|---|
| AU | 2019446955 A1 | 12/2021 | |
| CA | 3136633 A1 | 10/2020 | |
| CA | 3137393 A1 | 11/2020 | |
| CA | 3139082 A1 | 11/2020 | |
| CN | 113924098 A | 1/2022 | |
| CN | 113939276 A | 1/2022 | |
| CN | 114072945 A | 2/2022 | |
| EP | 3952840 A1 | 2/2022 | |
| EP | 3962488 A1 | 3/2022 | |
| WO | 2006058022 A1 | 6/2006 | |
| WO | 2007061454 A1 | 5/2007 | |
| WO | 2014018563 A3 | 5/2014 | |
| WO | WO-2017151723 A1 * | 9/2017 | A61K 31/122 |
| WO | 2020209872 A1 | 10/2020 | |
| WO | 2020222799 A1 | 11/2020 | |
| WO | 2020236159 A1 | 11/2020 | |
| WO | 2021242235 A1 | 12/2021 | |
| WO | 2021242297 A1 | 12/2021 | |
| WO | 2021262196 A1 | 12/2021 | |

OTHER PUBLICATIONS

Galatowicz, G, Ajayi Y, Stern ME, Calder VL. Ocular antiallergic compounds selectively inhibit human mast cell cytokines in vitro and conjunctival cell infiltration in vivo. Clin Exp Allergy. 2007; 37:1648-1656.

Hashiro et al. "A Combination Therapy of Psychotropic Drugs and Antihistaminics or Antiallergics in Patients with Chronic Urticaria". Journal of Dermatological Sciences, 1996; 11:209-213.

Koyama, Katsushi et al. 2002. Efficacy of Methylcobalamin on Lowing Total Homocysteine Plasma Concentrations in Haemodialysis Patients Receiving High-dose Folic Acid Supplementation. Nephrol Dial Transplant, 2002, 16: 911-22.

Leon, Michael, Sawmiller, Darrell, Shytle, R. Douglas, and Tan, Jun. 2018. Therapeutic Cocktail Approach for Treatment of Hyperhomocysteinemia in Alzheimer's Disease. Cell Med. 2018; 10: 2155179017722280.

Naddafi, F., Mirshafiey A., The neglected role of histamine in Alzheimer's disease., Jun. 2013;28(4):327-36. doi 10.1177/1533317513488925. Epub May 15, 2013.

Niazi, Sarfaraz K., Handbook of Pharmaceutical Manufacturing Formulations, 2nd Edition, vols. 1-6, 2009.

Riethmuller et al. Arzneimittel-Forschung, 1994, vol. 44, No. 10, pp. 1136-1140.

Sedeyn, Jonathan Histamine Induces Alzheimer's Disease-Like Blood Brain Barrier Breach and local cellular Responses in Mouse Brain Organotypic Culture. Hindawi. Aug. 21, 2015.

Simons, F.E., Simons, K.J. Clinical pharmacology of new histamine H1 receptor antagonist. Clin Pharmacokinet. 1999;36:329-352.

Smith, A. David, et al, 2010. Homocysteine-Lowering by B Vitamins Slows the Rate of Accelerated Brain Atrophy in Mild Cognitive Impairment: A Randomized Controlled Trial. Plos One, Sep. 2010, vol. 5, Issue 9, e12244.

St-Jean, Genevieve; Turcotte, Isabelle; Bastien, Celyne H. Cerebral asymmetry in insomnia sufferers. Frontiers in Neurology 2012, 3, 1-12.

Szelenyi, I., Achterrath-Tuckermann, U., Schmidt, J., Minker, E., Paegelow, I., Werner, H. Azelastine: A multifaceted drug for asthma therapy. Agents Actions Suppl. 1991;34:295-311. (abstract).

Tanaka, Hibiki, Hashimoto, Mamoru, et al, 2015. Relationship Between Dementia Severity and Behavioural and Psychological Symptoms in Early-Onset Alzheimer's Disease. Psychogeriatrics. Dec. 2015;15(4):242-7.

Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.

Yoneda, Kazunori, et al. 1997, Suppression by Azelastine Hydrochloride of NF-KB Activation Involved in Generation of Cytokines and Nitric Oxide. Japanese Journal of Pharmacology, 73:145-53.

Zhang, Yiting et al. 2016. Decreased Brain Levels of Vitamin B12 in Aging, Autism and Schizophrenia. Plos One, 0146797 Jan. 22, 2016.

Co-Pending U.S. Appl. No. 16/382,885, Response to Jun. 5, 2020 Final office action filed Jul. 31, 2020, 9 pages.

(Wang, Jianmin) Co-Pending U.S. Appl. No. 16/382,885, filed Apr. 12, 2019, Specification and claims.

(Wang, Jianmin) Co-Pending U.S. Appl. No. 16/398,845, filed Apr. 30, 2019, Specification and Claims.

(Wang, Jianmin) Co-Pending U.S. Appl. No. 16/418,614, filed May 21, 2019, Specification and Claims.

(Wang, Jianmin) Co-pending U.S. Appl. No. 16/424,788, filed May 29, 2019, Specification and Claims.

(Wang, Jianmin) Co-Pending U.S. Appl. No. 16/426,121, filed May 30, 2019, Specification and Claims.

(Wang, Jianmin) Co-Pending U.S. Appl. No. 16/831,330), filed Mar. 26, 2020, Specification and Claims.

(Wang, Jianmin) Co-Pending U.S. Appl. No. 16/834,146, filed Mar. 30, 2020, Specification and Claims.

(Wang, Jianmin) Co-Pending U.S. Appl. No. 16/884,459, filed May 27, 2020, Specification and Claims.

(Wang, Jianmin) Co-Pending U.S. Appl. No. 16/884,553, filed May 27, 2020, Specification and Claims.

(Wang, Jianmin) Co-Pending Application No. PCT/US19/29885, filed Apr. 30, 2019, Specification and Claims.

(Wang, Jianmin) Co-Pending Application No. PCT/US19/33359, Filed May 21, 2019, Specification and Claims.

(Wang, Jianmin) Co-Pending Application No. PCT/US20/39916, Filed Jun. 26, 2020, Specification and Claims.

(Wang, Jianmin) Co-Pending Application No. PCT/US2019/027293, filed Apr. 12, 2019, Specification and Claims.

Aisen, Paul S., et al. 2008. High Dose B Vitamin Supplementation and Cognitive Decline in Alzheimer's Disease: A Randomized Controlled Trial. JAMA. Oct. 15, 2008; 300(15): 1774-1783.

Bezprozvanny, Ilya. The rise and fall of Dimebon. National Institute of Health. Feb. 12, 2014.

Calderon-Ospina, Carlos Alberto, NAVA, Mauricio Orlando, 2020. B Vitamins in thenervous system: Current knowledge of the biochemical modes of action and synergies of thiamine,pyridoxine, and cobalamin. CNS Neurosci Ther. 2020; 26:5-13.

Casale, T. B. The interaction of azelastine with human lung histamine H1, beta, and muscarinic receptor-binding sites. J Allergy Clin Immunol. 1989;83:771-776.

Category H1 receptor antagonists. Wikipedia. Sep. 20, 2012.

Ciprandi, G., Pronzato, C., Passalacqua, G., et al. Topical azelastine reduces eosinophil activation and intercellular adhesion molecule-1 expression on nasal epithelial cells: An antiallergic activity. J Allergy Clin Immunol. 1996;98(6 Pt 1):1088-1096.

Co-Pending U.S. Appl. No. 16/382,885, Final office action dated Jun. 5, 2020, 13 pgs.

Co-Pending U.S. Appl. No. 16/382,885, Non-Final office action and list of references dated Nov. 29, 2019, 23 pgs.

(56) References Cited

OTHER PUBLICATIONS

Co-Pending U.S. Appl. No. 16/382,885, Response to Nov. 29, 2019 Non-Final office action filed Mar. 2, 2020.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Interview Summary dated Dec. 18, 2019, 7 pages.
Co-Pending U.S. Appl. No. 16/398,845, Non-Final Office Action dated Aug. 6, 2019, 25 pages.
Co-Pending U.S. Appl. No. 16/398,845, Notice of Allowance dated Jan. 21, 2020, 11 pages.
Co-Pending U.S. Appl. No. 16/398,845, Response to Non-Final Office Action dated Nov. 3, 2019, 9 pages.
Co-Pending U.S. Appl. No. 16/418,614, Interview Summary dated Dec. 18, 2019, 7 pages.
Co-Pending U.S. Appl. No. 16/418,614, Non-Final Office Action dated Aug. 6, 2019, 31 pages.
Co-Pending U.S. Appl. No. 16/418,614, Notice of Allowance dated Jan. 30, 2020, 12 pages.
Co-Pending U.S. Appl. No. 16/418,614, Response to Non-Final Office Action dated Nov. 3, 2019, 10 pages.
Co-Pending U.S. Appl. No. 16/424,788 Non-Final Office Action, dated Nov. 29, 2019, 24 pgs.
Co-Pending U.S. Appl. No. 16/424,788 Response to Nov. 29, 2019 Non-Final Office Action, filed Mar. 2, 2020.
Co-Pending U.S. Appl. No. 16/424,788 Response to Restriction Requirement, dated Oct. 2, 2019, 3 pgs.
Co-pending U.S. Appl. No. 16/424,788 Restriction Requirement, dated Aug. 9, 2019, 7 pgs.
Co-Pending U.S. Appl. No. 16/426,121, Non-Final Office Action dated Aug. 6, 2019, 25 pages.
Co-Pending U.S. Appl. No. 16/426,121, Notice of allowance dated Jan. 21, 2020, 18 pages.
Co-Pending U.S. Appl. No. 16/426,121, Response to Non-Final Office Action dated Nov. 6, 2019, 9 pages.
Co-pending application No. PCT/US19/29885 International Search Report dated Jul. 15, 2019. 7 pages.
Co-pending application No. PCT/US19/33359 International Search Report and Written Opinior dated Aug. 15, 2019. 9 pages.
Co-Pending Application No. PCT/US2019/027293, Search Report & Written Opinion, dated Sep. 17, 2019, 8 pages.
Goedert, M., Spillantini, M.G,. 2006. A century of Alzheimer's disease. Science, 314:777-81.
Grober, Uwe, Kisters, Klaus, and Schmidt, Joachim, 2013. Neuroenhancement with Vitamin B12—Underestimated Neurological Significance. Nutrients, 2013, 5, 5031-5045.
Hansen et al. Clinical Interventions in Aging 2008, vol. 3, No. 2, pp. 211-225.
Hatakeyama, AikO, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).
Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.
JK, Gupta and Sana, Qureshi Shaiba, 2015. Potential Benefits of Methylcobalamin: Austin J. Pharmacol. Ther. vol. 3, Issue 3, 2015.
Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.
Kobe, Theresa, et al. 2016. Vitamin B-12 concentration, memory performance, and hippocampal structure in patients with mild cognitive impairment. American Journal of Clinical. Nutrition, 2016; 103:1045-54.

(Wang, Jianmin) Co-Pending U.S. Appl. No. 17/094,405, filed Nov. 10, 2020, Specification and Claims.
(Wang, Jianmin) Co-Pending Application No. PCT/US20/34735, filed May 27, 2020, Specification and Claims.
(Wang, Jianmin) Co-Pending Application No. PCT/US20/59846, filed Nov. 10, 2020, Specification and figures.
Co-Pending U.S. Appl. No. 16/382,885, Non-Final office action dated Dec. 22, 2020, 19 pgs.
Co-Pending U.S. Appl. No. 16/382,885, Response to Dec. 22, 2020 Non-Final office action filed Jan. 21, 2021, 7 pgs.
Co-Pending U.S. Appl. No. 16/424,788 Corrected Notice of Allowance, dated Jan. 7, 2021, 5 pages.
Co-Pending U.S. Appl. No. 16/424,788 Non-Final Office Action, dated Nov. 5, 2020, 8 pgs.
Co-Pending U.S. Appl. No. 16/424,788 Notice of Allowance, dated Dec. 17, 2020, 9 pages.
Co-Pending U.S. Appl. No. 16/424,788 Response to Nov. 5, 2020 Non-Final Office Action, dated Dec. 2, 2020, 6 pages.
Co-Pending U.S. Appl. No. 16/426,121, Interview Summary dated Dec. 18, 2019, 7 pages.
Co-Pending U.S. Appl. No. 16/884,459, filed Dec. 15, 2020 Final Office Action, 15 pages.
Co-Pending U.S. Appl. No. 16/884,459, Response to Aug. 11, 2020 Non-Final Office Action dated Nov. 12, 2020, 11 pages.
Co-Pending U.S. Appl. No. 16/884,553, Notice of Allowance dated Dec. 2, 2020, 9 pages.
Co-Pending U.S. Appl. No. 16/884,553, Response to Aug. 11, 2020 Non-Final Office Action dated Nov. 12, 2020, 8 pages.
Co-Pending U.S. Appl. No. 17/094,405, Restriction Requirement dated Jan. 26, 2021, 5 pages.
Co-Pending Application No. PCT/US20/34735, International Search Report and Written Opinion dated Aug. 17, 2020, 10 pages.
Co-Pending Application No. PCT/US20/39916, International Search Report and Written Opinion dated Oct. 8, 2020, 8 pages.
Co-Pending Application No. PCT/US2019/027293, Corrected Written Opinion, dated Oct. 29, 2019, 5 pages.
Gupta, J. K. et al. Potential Benefits of Methylcobalamin: A Review. Oct. 8, 2015, Austin J Pharmacol Ther, vol. 3, Issue 3, 5 pages.
Starkstein, et al., "The construct of generalized anxiety disorder in altheimer's disease," Am J Geriatr Psychiatry Jan. 2007 15(1) 42-49.
Co-Pending U.S. Appl. No. 16/382,885, Notice of Allowance dated Feb. 10, 2021, 9 pages.
Co-Pending U.S. Appl. No. 16/831,330, Non-Final Office Action dated Apr. 7, 2021, 16 pages.
Co-Pending U.S. Appl. No. 16/884,459, Response to Dec. 15, 2020 Final Office Action, filed Mar. 15, 2021, 30 pages.
Co-Pending U.S. Appl. No. 17/094,405, Non-Final Office Action dated Apr. 14, 2021, 21 pages.
Co-Pending U.S. Appl. No. 17/094,405, Response to Jan. 26, 2021 Restriction Requirement, filed Apr. 5, 2021, 7 pages.
Co-Pending Application No. PCT/US20/59846, International Search Report and Written Opinion dated Mar. 8, 2021, 8 pages.
Horak, Friedrich, "Effectiveness of twice daily azelastine nasal spray in patients with seasonal allergic rhinitis," Ther. Clin. Risk Manag., Oct. 2008; 4(5): 1009-1022.
Co-Pending U.S. Appl. No. 16/831,330, Response to Apr. 7, 2021 Non-Final Office Action filed Jul. 21, 2021, 7 pages.
Co-Pending U.S. Appl. No. 17/094,405, Response to Apr. 14, 2021 Non-Final Office Action filed Jul. 14, 2021, 7 pages.
(Wang, Jianmin) Co-Pending U.S. Appl. No. 17/394,898, filed Aug. 5, 2021, Specification and Claims.
Catena-Dell'Osso, M. et al., 2011, Inflammatory and Neurodegenerative Pathways in Depression: A New Avenue for Antidepressant Development? Curr Med Chem. 18 (2), 245-55, Abstract, 2 pages.
Co-Pending U.S. Appl. No. 16/831,330, Notice of Allowance dated Aug. 3, 2021, 8 pages.
Co-Pending U.S. Appl. No. 16/884,459, Non-Final Office Action dated Sep. 14, 2021, 35 pages.
Co-Pending U.S. Appl. No. 17/094,405, Final Office Action dated Jul. 30, 2021, 22 pages.
Co-Pending U.S. Appl. No. 17/094,405, Response to Jul. 30, 2021 Final Office Action, dated Sep. 30, 2021, 10 pages.

(56) References Cited

OTHER PUBLICATIONS

Co-Pending U.S. Appl. No. 17/394,898, Response to Oct. 21, 2021 Restriction Requirement, dated Nov. 10, 2021, 2 pages.
Co-Pending U.S. Appl. No. 17/394,898, Restriction Requirement dated Oct. 21, 2021, 9 pages.
Co-Pending U.S. Appl. No. 17/459,868, Preliminary Amendment, filed Aug. 27, 2021, 8 pages.
Reynolds, Edward, "Vitamin B12, folic acid, and the nervous system", The Lancet Neurology, Nov. 2006, Abstract, 35 pages.
(Wang, Jianmin) Co-Pending U.S. Appl. No. 17/459,868, filed Aug. 27, 2021, Specification and Claims.
(Wang, Jianmin) Co-Pending U.S. Appl. No. 17/546,342, filed Dec. 9, 2021, Specification and Claims.
(Wang, Jianmin) Co-Pending U.S. Appl. No. 17/673,136, filed Feb. 16, 2022, Specification and Claims.
(Wang, Jianmin) Co-Pending Application No. PCT/US21/44654, filed Aug. 5, 2021, Specification and Claims.
(Wang, Jianmin) Co-Pending Application No. PCT/US22/16545, filed Feb. 16, 2022, Specification and Claims.
(Wang, Jianmin) Co-Pending Australia National Stage Application No. 2019443520, Effective Filing Date Apr. 30, 2019, Specification and Claims (See PCT/US19/29885, which published as WO 2020/222799, for Specification and Claims as filed—See copy submitted with Feb. 5, 2021 IDS).
(Wang, Jianmin) Co-Pending Australia National Stage Application No. 2019445048, Effective Filing Date Apr. 12, 2019, Specification and Claims (See PCT/US19/27293, which published as WO 2020/209872, for Specification and Claims as filed—See copy submitted with Feb. 5, 2021 IDS).
(Wang, Jianmin) Co-Pending Australia National Stage Application No. 2019446955, Effective Filing Date May 21, 2019, Specification and Claims (See PCT/US19/33359, which published as WO2020/236159, for Specification and Claims as filed—See copy submitted with Feb. 5, 2021 IDS).
(Wang, Jianmin) Co-Pending Canada National Stage Application No. 3,136,633, filed Oct. 3, 2021, Specification and Claims, 25 pages.
(Wang, Jianmin) Co-Pending Canada National Stage Application No. 3,137,393, Filed Oct. 19, 2021, Specification and Claims, 17 pages.
(Wang, Jianmin) Co-Pending Canada National Stage Application No. 3,139,082, Filed Nov. 3, 2021, Claims and Amended Specification, 25 pages.
(Wang, Jianmin) Co-Pending China National Stage Application No. 201980095322.X, filed Oct. 11, 2021, Specification and Claims (32 pages) (see PCT/US19/27293, which published as WO2020/209872 for English Translation—See copy submitted with Feb. 5, 2021 IDS).
(Wang, Jianmin) Co-Pending China National Stage Application No. 201980095741.3, Filed Oct. 25, 2021, Specification and Amended Claims as filed (26 pages) with English Translation of the Amended Claims (2 pages) (See PCT/US19/29885, which published as WO 2020/222799, for English Translation of the Specification—See copy submitted with Feb. 5, 2021 IDS).
(Wang, Jianmin) Co-Pending China National Stage Application No. 201980096574.4, Filed Nov. 18, 2021, Specification and Amended Claims as filed (48 pages) with English Translation of the Amended Claims (4 pages) (See PCT/US19/33359, which published as WO2020/236159, for English Translation of the Specification—See copy submitted with Feb. 5, 2021 IDS).
(Wang, Jianmin) Co-Pending European National Stage Application No. 19924315.5, filed Nov. 11, 2021, Specification and Amended Claims as filed (34 pages).
(Wang, Jianmin) Co-Pending European National Stage Application No. 19927207.1, filed Nov. 29, 2021, Specification and Amended Claims as filed (26 pages).
(Wang, Jianmin) Co-Pending European National Stage Application No. 19929933.0, filed Dec. 21, 2021, Specification and Amended Claims as filed (35 pages).
(Wang, Jianmin) Co-Pending Japan National Stage Application No. 2021-556914, filed Sep. 17, 2021, Specification and Claims (19 pages) (see PCT/US19/27293, which published as WO 2020/209872, for English Translation—See copy submitted with Feb. 5, 2021 IDS).
(Wang, Jianmin) Co-Pending Japan National Stage Application No. 2021-558496, filed Sep. 21, 2021, Specification and Claims (15 pages) (See PCT/US19/29885, which published as WO 2020/222799, for English Translation—See copy submitted with Feb. 5, 2021 IDS).
(Wang, Jianmin) Co-Pending Japan National Stage Application No. 2021-566489, filed Nov. 9, 2021, Request for Entry and Specification and Claims (18 pages) (See PCT/US19/33359, which published as WO2020/236159, for English Translation of Specification and Claims—See copy submitted with Feb. 5, 2021 IDS).
Co-Pending U.S. Appl. No. 16/834,146, Non-Final Office Action dated Nov. 15, 2021, 29 pages.
Co-Pending U.S. Appl. No. 16/834,146, Response to Nov. 15, 2021 Non-Final Office Action, dated Feb. 22, 2022, 9 pages.
Co-Pending U.S. Appl. No. 16/884,459, Final Office Action dated Dec. 10, 2021, 19 pages.
Co-Pending U.S. Appl. No. 16/884,459, Response to Dec. 10, 2021 Final Office Action, filed Feb. 25, 2022, 18 pages.
Co-Pending U.S. Appl. No. 16/884,459, Response to Sep. 14, 2021 Non-Final Office Action, filed Nov. 16, 2021, 9 pages.
Co-Pending U.S. Appl. No. 16/884,459, Rule 132 Declaration dated Feb. 24, 2022, 4 pages.
Co-Pending U.S. Appl. No. 17/394,898, Non-Final Office Action dated Nov. 24, 2021, 9 pages.
Co-Pending U.S. Appl. No. 17/394,898, Response to Nov. 24, 2021 Non-Final Office Action, dated Feb. 23, 2022, 9 pages.
Co-Pending Application No. PCT/US21/44654, International Search Report and Written Opinion, dated Nov. 15, 2021, 10 pages.
Co-Pending China National Stage Application No. 201980095322.X, English Version of Amended Claims as filed Oct. 11, 2021, 3 pages.
Munoz-Cano et al. "Severity of Allergic Rhinitis Impacts Sleep and Anxiety: Results from a Large Spanish Cohort". Clinical and Translational Allergy, 2018, 8 (Article 23), p. 1-9.
Co-Pending U.S. Appl. No. 16/834,146, Final Office Action dated Mar. 18, 2022, 20 pages.
Co-Pending U.S. Appl. No. 17/394,898, Examiner-Initiated Interview Summary for Interview conducted Mar. 4, 2022, 1 page.
Co-Pending U.S. Appl. No. 17/394,898, Notice of Allowance and Examiner's Amendment dated Mar. 17, 2022, 13 pages.

* cited by examiner

COMPOSITIONS AND METHODS FOR TREATING ALZHEIMER'S DISEASE AND PARKINSON'S DISEASE

CROSS-REFERENCE TO RELATED APPLICATIONS

The present application is a Continuation in Part application of U.S. patent application Ser. No. 16/382,885 filed on Apr. 12, 2019, the disclosure of which is hereby incorporated by reference herein in its entirety.

FIELD OF THE INVENTION

The present invention relates to the field of practical medicine, namely, to the use of pharmaceutical compositions for treatment of Alzheimer's disease and Parkinson's disease. More specifically, the invention relates to novel combinations of compounds which can effectively treat Alzheimer's disease (AD) and Parkinson's disease (PD).

BACKGROUND OF THE INVENTION

Alzheimer's disease (AD) is a progressive, chronic neurodegenerative disease that usually starts slowly and gradually worsens over time. AD is the most common cause of dementia among older adults. Dementia is the loss of cognitive functioning—thinking, remembering, and reasoning—and behavioral abilities to such an extent that it interferes with a person's daily life and activities. In its early stages, memory loss is mild, but with late-stage AD, individuals lose the ability to carry on a conversation and respond to their environment. If untreated, AD ultimately leads to death. Although the speed of progression can vary, the typical life expectancy following diagnosis is three to nine years.

Neuropathologically, AD is characterized by accumulation of neurotic plaques of amyloid beta protein (Aβ) and neurofibrillary tangles of hyperphosphorylated tau protein (p-tau). The bulk of current evidence points to Aβ accumulation as a critical primary causative factor in sporadic AD. So far, all promising approaches for decreasing Aβ or p-tau levels including mechanisms such as inhibition of Aβ or p-tau generation, reduction of soluble Aβ levels and enhancement of Aβ or p-tau clearance from the CNS have not provided desired outcomes from their clinical trials. While development of Aβ based treatments follows logically from known Aβ mechanisms, a number of factors might limit the effectiveness of such treatments if applied in isolation. But more importantly, a number of other potential mechanisms might constitute important causative factors in AD. Such non-Aβ mechanisms might play even larger roles, or perhaps synergistic roles, as the disease progresses. Thus, it is likely that parallel application of neuroprotective strategies will play a vital role in delaying AD onset and slowing AD progression.

Homocysteine is a sulfur amino acid involved in essential metabolic pathways, including methylation reactions. Elevation of homocysteine in blood is a marker of genetic disorders and deficiencies of vitamins B12. Homocysteine elevation is associated with vascular disease, neuropsychiatric disorders, neurovascular ischemic disease, including stroke, silent infarctions and white matter disease. Studies have linked homocysteine to amyloid and glutamate neurotoxicity, and to cognitive dysfunction and AD. For example, homocysteine elevation induces hippocampal neuron loss in transgenic mice with brain amyloid deposition. Studies also have demonstrated a relationship between plasma homocysteine level and AD and cognitive function in non-demented individuals. This relationship spans the normal range of homocysteine levels. Reduction of homocysteine levels can be readily achieved with high doses of vitamin B12, and could plausibly represent a disease-modifying intervention in AD.

Methylcobalamin, one of two active forms of four vitamin B12 vitamers, compared with other analogs, is the most effective in being up-taken by subcellular organelles of neurons. Therefore, methylcobalamin in combination with azelastine may provide a better treatment option for nervous disorders such as AD.

On the other hand, the genetic, cellular, and molecular changes associated with AD support the evidence that activated immune and inflammatory processes is a part of the disease. Also, a strong benefit of long-term use of NSAIDs was shown in epidemiological studies. So, it is generally accepted that AD is partially an inflammatory disease and that inhibiting inflammation is an option of treating AD.

Inflammation clearly occurs in pathologically vulnerable regions of the AD brain, and it does so with the full complexity of local peripheral inflammatory responses. In the periphery, degenerating tissue and the deposition of highly insoluble abnormal materials are classical stimulants of inflammation. Likewise, in the AD brain, damaged neurons and neurites and highly insoluble amyloid β peptide deposits and neurofibrillary tangles provide obvious stimuli for inflammation. Because these stimuli are discrete, micro-localized, and present from early preclinical to terminal stages of AD, local upregulation of complement, cytokines, acute phase reactants, and other inflammatory mediators is also discrete, micro-localized, and chronic. Cumulated over many years, direct and bystander damage from AD inflammatory mechanisms is likely to significantly exacerbate the very pathogenic processes that gave rise to it. Thus, animal models and clinical studies so far strongly suggest that AD inflammation significantly contributes to AD pathogenesis. By better understanding AD inflammatory and immune-regulatory processes, it should be possible to develop anti-inflammatory approaches that may reverse or delay or prevent developing of this devastating disorder.

Azelastine is classified pharmacologically as a second-generation antihistamine and is a relatively selective, non-sedating, competitive antagonist at H1 receptors. More uniquely, its inhibition of inflammatory mediators, in addition to antihistaminic and mast cell stabilizing effects, places it among the new generation of dual-acting anti-inflammatory drugs. In addition to azelastine's high affinity for H1 receptors, its ability to modify several other mediators of inflammation and allergy contributes to its mechanism of action. In vitro and in vivo studies, as well as clinical trials support the dual effects of direct inhibition and stabilization of inflammatory cells. In vitro data indicate that azelastine's affinity for H1 receptors is estimated to be several times greater than that of chlorpheniramine, a first-generation H1 antagonist. Azelastine has only weak affinity for H2 receptors. Release of histamine from mast cells is also inhibited possibly by reversible inhibition of voltage-dependent L-type calcium channels. Inhibition of mast cell degranulation may also decrease the release of other inflammatory mediators, including leukotrienes and interleukin-1β, among others. Azelastine also directly antagonizes other mediators of inflammation, such as tumor necrosis factor-α, leukotrienes, endothelin-1, and platelet-activating factor.

Therefore, a unique combination of azelastine (antihistamine agent with anti-inflammatory activities) with methylcobalamin (for maintaining myelin synthesis, neuronal metabolism, and neuronal regeneration in the nervon system) would potentially be, in terms of working through multi-mechanisms of actions, an effective treatment for AD patients.

SUMMARY OF THE INVENTION

The present invention includes a pharmaceutical composition that comprises two active pharmaceutical ingredients. This pharmaceutical composition comprises the first active ingredient that is azelastine or a pharmaceutically acceptable salt of azelastine and the second active ingredient that is methylcobalamin.

In some embodiments of this invention, the pharmaceutically acceptable salt of azelastine in the pharmaceutical composition is azelastine hydrochloride.

In some embodiments of this invention, azelastine hydrochloride (and/or other salt thereof) in the pharmaceutical composition is provided in an amount of about 8 mg to about 24 mg and methylcobalamin in an amount of about 0.5 mg to about 50 mg.

The present invention also includes an oral pharmaceutical dosage form of the pharmaceutical composition that is a solid, liquid, gel, or solution form.

The present invention further includes the medical use of the oral pharmaceutical dosage form of the pharmaceutical composition through administration of the dosage form to patients with Alzheimer's disease or Parkinson's disease.

In some embodiments of this invention, an oral pharmaceutical dosage form of the pharmaceutical composition containing azelastine hydrochloride (and/or other salt thereof) in an amount of about 8 mg to about 24 mg and methylcobalamin in an amount of about 0.5 mg to about 50 mg is administered to patients with Alzheimer's disease or Parkinson's disease.

Included in embodiments of the invention is Aspect 1, which encompasses a pharmaceutical composition, comprising azelastine or a pharmaceutically acceptable salt of azelastine, methylcobalamin, and one or more pharmaceutically acceptable excipients.

Aspect 2 is the pharmaceutical composition of Aspect 1, wherein the azelastine or the pharmaceutically acceptable salt of azelastine is present in the pharmaceutical composition in an amount in the range of about 8 mg to about 24 mg, such as about 8 mg to about 18 mg, or about 12 mg to about 16 mg, or about 12 mg, or about 8 mg to about 24 mg, or about 8 mg, or about 8 mg to about 22 mg, or about 10 mg to about 20 mg, or about 10 mg to about 16 mg, or about 10 mg to about 12 mg, or about 12 mg to about 20 mg, or about 8 mg to about 12 mg, or any range in between any of these endpoints.

Aspect 3 is the pharmaceutical composition of Aspect 1 or 2, wherein the methylcobalamin is present in the pharmaceutical composition in an amount in the range of about 0.5 mg to about 50 mg, such as about 0.5 mg to about 45 mg, or about 0.5 mg to about 35 mg, or about 1 mg to about 10 mg, or about 0.5 mg to about 5 mg, or about 0.5 mg to about 20 mg, or up to about 25 mg, or up to about 15 mg, or up to about 8 mg, or up to about 5 mg, or about 5 mg to about 12 mg, or about 2 mg to about 8 mg, or about 1 mg, or any range in between any of these endpoints.

Aspect 4 is the pharmaceutical composition of any of Aspects 1-3, wherein the methylcobalamin is present in the pharmaceutical composition in an amount in the range of about 0.5 mg to about 10 mg.

Aspect 5 is the pharmaceutical composition of any of Aspects 1-4, wherein in the pharmaceutical composition the azelastine or the pharmaceutically acceptable salt of azelastine is present in an amount in the range of about 8 mg to about 24 mg and the methylcobalamin is present in an amount in the range of about 0.5 mg to about 50 mg.

Aspect 6 is the pharmaceutical composition of any of Aspects 1-5, wherein the pharmaceutically acceptable salt of azelastine is azelastine hydrochloride.

Aspect 7 is the pharmaceutical composition of any of Aspects 1-6, wherein the methylcobalamin is present in the pharmaceutical composition in an amount in the range of about 0.5 mg to about 50 mg.

Aspect 8 is the pharmaceutical composition of any of Aspects 1-7, wherein the azelastine hydrochloride is present in an amount in the range of about 8 mg to about 18 mg.

Aspect 9 is the pharmaceutical composition of any of Aspects 1-8, wherein the pharmaceutical composition is formulated as an oral pharmaceutical dosage form.

Aspect 10 is the pharmaceutical composition of any of Aspects 1-9, wherein the oral pharmaceutical dosage form is a solid form or a liquid form.

Aspect 11 is the pharmaceutical composition of any of Aspects 1-10, wherein the azelastine hydrochloride is present in the pharmaceutical composition in an amount ranging from about 8 mg to about 12 mg and the amount of methylcobalamin is present in the pharmaceutical composition in an amount ranging from about 1 mg to about 5 mg.

Aspect 12 is a method of treating a patient with Alzheimer's disease or Parkinson's disease, comprising administering to the patient an effective amount of a pharmaceutical composition comprising azelastine or a pharmaceutically acceptable salt of azelastine, methylcobalamin, and one or more pharmaceutically acceptable excipients for a period of time sufficient to alleviate, reduce, prevent and/or eliminate one or more symptoms of the patient's Alzheimer's disease and/or Parkinson's disease.

Aspect 13 is the method of any of Aspects 1-12, wherein the pharmaceutical composition is administered to the patient once or twice a day, or three times a day, or once every 2 or 3 or 4 days in an oral solid or liquid form.

Aspect 14 is the method of any of Aspects 1-13, wherein the azelastine or the pharmaceutically acceptable salt of azelastine is present in the pharmaceutical composition in an amount in the range of about 8 mg to about 24 mg.

Aspect 15 is the method of any of Aspects 1-14, wherein the methylcobalamin is present in the composition in an amount in the range of about 0.5 mg to about 50 mg.

Aspect 16 is the method of any of Aspects 1-15, wherein the pharmaceutical composition is administered to the patient for a period of at least 6 weeks.

Aspect 17 is the method of any of Aspects 1-16, wherein the methylcobalamin is present in the pharmaceutical composition in an amount in the range of about 0.5 mg to 10 mg.

Aspect 18 is the method of any of Aspects 1-17, wherein the methylcobalamin is present in the pharmaceutical composition in an amount in the range of about 1 mg to about 10 mg.

Aspect 19 is the method of any of Aspects 1-18, wherein in the pharmaceutical composition the pharmaceutically acceptable salt of azelastine is azelastine hydrochloride and is present in an amount in the range of about 8 mg to about 24 mg and the methylcobalamin is present in an amount in the range of about 0.5 mg to about 50 mg.

Aspect 20 is the method of any of Aspects 1-19, wherein the methylcobalamin is present in the composition in an amount in the range of about 0.5 mg to about 10 mg.

DETAILED DESCRIPTION OF THE INVENTION

Through clinical practice, the inventors of the present invention found that a pharmaceutical composition with oral dosage forms comprising the active agents, a salt form of azelastine and methylcobalamin, would be a treatment which can slow or even stop the progression of Alzheimer's disease or Parkinson's disease.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

As used herein, the term "methylcobalamin" refers to a cobalamin, a form of vitamin B12, co-methylcobalamin, also, means MeCbl, mecobalamin, mecobalamina, mecobalaminum, or methyl vitamin B12.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine, including in the solid oral dosage forms, are to the amounts and dosage ranges of azelastine hydrochloride.

As used herein, the term "salt" refers to a salt of azelastine formed with an acid selected from a group of acids consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be via capsule, tablet, gel, spray, drops, solution, suspensions, syrups, or the like.

The term "about" used herein in the context of quantitative measurements means the indicated amount ±10%. For example, with a ±10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration, for example, admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the pharmaceutical composition with a pharmaceutical diluent which is inert and inserting this mixture into a hard gelatin capsule having the appropriate size. If soft capsules are desired, a slurry of the pharmaceutical composition with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure are usually administered orally. This disclosure therefore provides pharmaceutical compositions that comprise a solid dispersion comprising azelastine and methylcobalamin as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

Some examples of suitable excipients are described herein. When the pharmaceutical composition is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In embodiments, the pharmaceutical compositions can comprise a) about 8 mg-24 mg of azelastine, or azelastine HCl (or other salt thereof) and b) about 0.5 mg to 50 mg of methylcobalamin, or a) about 8 mg-18 mg of azelastine, or azelastine HCl (or other salt thereof) and b) about 0.5 mg to 10 mg of methylcobalamin, or a) about 12 mg-16 mg of azelastine, or azelastine HCl (or other salt thereof) and b) about 0.5 mg to 5 mg of methylcobalamin. For example, the compositions can comprise a) about 12 mg of azelastine, or azelastine HCl (or other salt thereof) and b) about 1 mg of methylcobalamin HCl, or a) about 8 mg to 24 mg azelastine, or azelastine HCl (or other salt thereof) and b) any amount of methylcobalamin.

In embodiments, the pharmaceutical compositions can comprise a) azelastine, or azelastine HCl (or other salt thereof) in an amount in the range of about 8 mg to about 22 mg, such as in the range of about 10 mg to about 20 mg, or about 10 mg to about 16 mg, or about 8 mg to about 18 mg, or about 10 mg to about 12 mg, or about 12 mg to about 20 mg, or about 8 mg to about 12 mg, or any range in between any of these endpoints, or any amount of azelastine, azelastine HCl (or other salt thereof) and b) methylcobalamin in an amount in the range of about 0.5 mg to about 50 mg, such as about 0.5 mg to about 45 mg, or about 0.5 mg to about 35 mg, or about 1 mg to about 10 mg, or about 0.5 mg to about 5 mg, or about 0.5 mg to about 20 mg, or up to about 25 mg, or up to about 15 mg, or up to about 8 mg, or up to about 5 mg, or about 5 mg to about 12 mg, or about 2 mg to about 8 mg, or about 1 mg, or any range in between any of these endpoints.

In embodiments, the amount of azelastine, or azelastine HCl (or other salt thereof) present in the composition can be equal to, more than, or less than the amount of methylcobalamin present in the composition. In embodiments, the amount of azelastine, or azelastine HCl (and/or other salt thereof) present in the composition can be 2 times as much, or 3 times as much, or 4, 5, 6, 7, 8, 9, 10, 15, 20, 25, 30, 35, 40, 45, 50, 75, or 100 times as much as the amount of methylcobalamin present in the composition, or vice versa, using any of the amounts disclosed above or claimed. Any one or more of the compositions of the invention can be used with any one or more the methods of the invention disclosed herein, or other methods of using the compositions.

It will be understood, that the amount of the pharmaceutical composition comprising azelastine HCl and methylcobalamin actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing azelastine HCl and methylcobalamin as described herein are administered to patients with Alzheimer's disease or Parkinson's disease, by oral administration once daily, twice daily, three times daily, four times daily, once every other day, once a week, two times a week, three times a week, four times a week, or five times a week, or combinations thereof. One of skill in the art will understand that the amounts of azelastine and methylcobalamin in the compositions as disclosed above or claimed can alternatively be the daily dosage amounts and can instead be formulated into single doses accordingly.

In embodiments, patients are administered with the pharmaceutical composition with a therapeutic effective daily dosage of azelastine HCl in the range of 8 mg to about 24 mg and methylcobalamin in an amount in the range of about 0.5 mg to about 50 mg.

In embodiments, the pharmaceutical dosage forms and tablets of pharmaceutical compositions containing azelastine, or azelastine HCl (or other salt thereof), and methylcobalamin as described herein are effective in slowing the progression or reversing symptoms of Alzheimer's disease or Parkinson's disease in about 2-16 weeks, such as within 2, 3, 4, 5, 6, 7, 8, 9, 10, 11, 12, 13, 14, 15, or 16 weeks, or any range in between. If Mini-Mental State Examination (MMSE) and Activities of Daily Living (ADL) are assessed for patients with AD or PD, the scores of MMSE and ADL can be improved by more than 50%.

The following Example is illustrative and should not be interpreted to limit the scope of the claimed subject matter.

Examples

A 70 year old patient with mid-stage Alzheimer's disease (AD) for 2 years and before treatment a baseline MMSE score of 12 and a Barthel Index (BI) of Activities of Daily Living score of 30, can be treated with a pharmaceutical composition of methylcobalamin and azelastine, e.g., a composition comprising methylcobalamin in an amount of 1.0 mg and azelastine, azelastine HCl or other salt thereof in an amount of 8 mg, up to twice daily (or any of the compositions described above or claimed, or for any treatment protocol or period of time described above or claimed). After 2 weeks, 3 weeks, 4 weeks, 5 weeks, 6 weeks, 7 weeks, 8 weeks, or more, one or more of his AD symptoms would be expected to improve by at least 10%, 20%, 30%, 40%, 50%, 60%, 70%, 80%, 90%, 100% or higher. For example, his MMSE score would be expected to improve from 12 to at least 22, which is an 83% improvement, and his BI score would be expected to improve from 30 to at least 80, which is a 167% improvement. This dramatic clinical outcome from this composition is unexpected for patients with AD and should be better than taking azelastine alone. Azelastine would reduce inflammation process of AD, by decreasing microglial activation, inhibiting expression of cytokines, counteracting reactive oxygen species and suppressing roles of nuclear factor kappa B in inflammatory process, to slow and may even stop neurodegeneration in AD. But in combination with azelastine, methylcobalamin, which promotes neuronal cell growth by facilitating myelin synthesis, nerve metabolism, and neuronal regeneration, maintains the effects of azelastine, and increases the reversion of symptoms of AD patients, thus the composition would create more effective and sustained treatment for AD patients.

A 70-year-old patient with Parkinson's disease (PD) for 3 years and before treatment a baseline Unified Parkinson's Disease Rating Scale (UPDRS) total score of 90 can be treated with a pharmaceutical composition of methylcobalamin and azelastine, e.g., a composition comprising methylcobalamin in an amount of 1.0 mg and azelastine, azelastine HCl or other salt thereof in an amount of 8 mg, up to twice daily (or any of the compositions described above or claimed, or for any treatment protocol or period of time described above or claimed). After 2 weeks, 3 weeks, 4 weeks, 5 weeks, 6 weeks, 7 weeks, 8 weeks, or more, one or more of his PD symptoms would be expected to improve by at least 10%, 20%, 30%, 40%, 50%, 60%, 70%, 80%, 90%, 100% or higher. For example, his UPDRS total score would be expected to improve from 90 to at least 40, which is a 56% improvement. Additionally, if the patient's MMSE score is evaluated, it would be expected to improve by over 50%.

REFERENCES

U.S. Pat. No. 9,919,050 (Mar. 20, 2018, Dang, et al); U.S. Pat. No. 9,901,585 (Feb. 27, 2018, Lulla, et al); U.S. Pat. No. 8,859,531 (Oct. 14, 2014, Lee, et al); U.S. Pat. No. 8,758,816 (Jun. 24, 2014, Fuge, et al); U.S. Pat. No. 8,318,709 (Nov. 27, 2012, Lulla, et al); U.S. Pat. No. 8,304,405 (Nov. 6, 2012, Lulla, et al); U.S. Pat. No. 8,168,620 (May 1, 2012, Lulla, et al); U.S. Pat. No. 8,071,073 (Dec. 6, 2011, Dang, et al); U.S. Pat. No. 7,022,687 (Apr. 4, 2006, Szelenyl, et al); U.S. Pat. No. 6,017,909 (Jan. 25, 2000, Hettche, et al); U.S. Pat. No. 5,994,357 (Nov. 30, 1999, Theoharides); U.S. Pat. No. 5,086,050 (Feb. 4, 1992, Hettche, et al); and U.S. Pat. No. 5,068,233 (Nov. 26, 1991, Achterrath-Tuckerman, et al.); U.S. Pat. No. 8,741,319 (Jun. 3, 2014, Crain et al); and U.S. Published Application Nos. 2010/0168053 (Kurtz); 2009/0012039 (Kurtz); and 2014/0127328 (Crain et al).

Carlos Alberto Calderon-Ospina, Mauricio Orlando Nava, 2020. B Vitamins in the nervous system: Current knowledge of the biochemical modes of action and synergies of thiamine, pyridoxine, and cobalamin. CNS Neurosci Ther. 2020; 26:5-13.

Katsushi, Koyoma et al. 2002. Efficacy of Methylcobalamin on Lowing Total Homocysteine Plasma Concentrations in Haemodialysis Patients Receiving High-dose Folic Acid Supplementation. Nephrol Dial Transplant, 2002, 16: 911-22.

Yiting Zhang, et al. 2016. Decreased Brain Levels of Vitamin B12 in Aging, Autism and Schizophrenia. PLOS ONE, 0146797 Jan. 22, 2016.

Theresa Kobe, et al. 2016. Vitamin B-12 concentration, memory performance, and hippocampal structure in patients with mild cognitive impairment. American Journal of Clinical. Nutrition, 2016; 103:1045-54.

Michael Leon, Darrell Sawmiller, R. Douglas Shytle, and Jun Tan, 2018. Therapeutic Cocktail Approach for Treatment of Hyperhomocysteinemia in Alzheimer's Disease. Cell Med. 2018; 10: 2155179017722280.

Paul S. Aisen, et al. 2008. High Dose B Vitamin Supplementation and Cognitive Decline in Alzheimer's Disease: A Randomized Controlled Trial. JAMA. 2008 Oct. 15; 300 (15): 1774-1783.

A. David Smith, et al, 2010. Homocysteine-Lowering by B Vitamins Slows the Rate of Accelerated Brain Atrophy in Mild Cognitive Impairment: A Randomized Controlled Trial. PLOS ONE, September 2010, Volume 5, Issue 9, e12244.

Uwe Grober, Klaus Kisters and Joachim Schmidt, 2013. Neuroenhancement with Vitamin B1—Underestimated Neurological Significance. Nutrients, 2013, 5, 5031-5045.

Gupta J K and Qureshi Shaiba Sana, 2015. Potential Benefits of Methylcobalamin: Austin J. Pharmacol. Ther. Volume 3, Issue 3, 2015.

Patricia B Williams, Elizabeth Crandall and John D Sheppard, 2010, Azelastine hydrochloride, a dual-acting anti-inflammatory ophthalmic solution, for treatment of allergic conjunctivitis. Clinical Ophthalmology, 2010:4 993-1001.

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Aiko Hatakeyama, et al, 2008, Azelastine hydrochloride on behavioral and psychological symptoms and activities of daily living in dementia patients. Geriatr Gerontol Int 2008; 8: 59-61.

Duraisamy Kempuraj, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 November 2003.

Kazunori Yoneda, et al. 1997, Suppression by Azelastine Hydrochloride of NF-KB Activation Involved in Generation of Cytokines and Nitric Oxide. Japanese Journal of Pharmacology, 73: 145-53.

Loyd Allen, Ansel's Pharmaceutical Dosage Forms and Drug Delivery Systems, Tenth (2013).

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method comprising:
    administering a pharmaceutical composition to a patient having Alzheimer's disease or Parkinson's disease:
    wherein the pharmaceutical composition comprises:
        an amount in the range of about 8 mg to about 24 mg of azelastine or of a pharmaceutically acceptable salt of azelastine;
        methylcobalamin;
        and one or more pharmaceutically acceptable excipients.

2. The method of claim 1, wherein the pharmaceutical composition is administered to the patient once or twice a day, or three times a day, or once every 2 or 3 or 4 days in an oral solid or liquid form.

3. The method of claim 1, wherein the methylcobalamin is present in the pharmaceutical composition in an amount in the range of about 0.5 mg to about 50 mg.

4. The method of claim 1, wherein the pharmaceutical composition is administered to the patient for a period of at least 6 weeks.

5. The method of claim 1, wherein the methylcobalamin is present in the pharmaceutical composition in an amount in the range of about 0.5 mg to 10 mg.

6. The method of claim 1, wherein the methylcobalamin is both present in the pharmaceutical composition and is present in an amount in the range of up to about 5 mg.

7. The method of claim 1, wherein:
    the azelastine or the pharmaceutically acceptable salt of azelastine is present in the pharmaceutical composition in an amount that is 2, 3, 4, 5, 6, 7, 8, 9, or 10 times as much as the methylcobalamin; or
    the methylcobalamin is present in the pharmaceutical composition in an amount that is 2, 3, 4, 5, 6, 7, 8, 9, or 10 times as much as the azelastine or the pharmaceutically acceptable salt of azelastine.

8. The method of claim 1, wherein the pharmaceutically acceptable salt of azelastine is azelastine hydrochloride.

9. The method of claim 1, wherein the pharmaceutical composition is administered to the patient in an oral liquid form.

10. The method of claim 1, wherein the pharmaceutical composition is a suspension, syrup, or elixir.

11. The method of claim 1, wherein the pharmaceutical composition is administered to the patient in an oral solid form.

12. The method of claim 1, wherein the pharmaceutical composition is a tablet, caplet, bi-layer tablet, film-coated tablet, pill, or capsule.

13. The method of claim 1, wherein the methylcobalamin is present in the pharmaceutical composition in an amount in the range of about 0.5 mg to about 2 mg.

14. The method of claim 1, wherein:
    the azelastine or the pharmaceutically acceptable salt of azelastine is present in the pharmaceutical composition in an amount in the range of about 8 mg to about 18 mg; and
    the methylcobalamin is present in the pharmaceutical composition in an amount in the range of about 1 mg to about 5 mg.

* * * * *